(12) United States Patent
Bollin

(10) Patent No.: US 11,092,528 B2
(45) Date of Patent: Aug. 17, 2021

(54) DEVICE AND METHOD FOR CALIBRATING AND CORRELATING SLUMP IN A CONCRETE MIXER

(71) Applicant: Neil Edward Bollin, Checotah, OK (US)

(72) Inventor: Neil Edward Bollin, Checotah, OK (US)

( * ) Notice: Subject to any disclaimer, the term of this patent is extended or adjusted under 35 U.S.C. 154(b) by 0 days.

(21) Appl. No.: 17/120,202

(22) Filed: Dec. 13, 2020

(65) Prior Publication Data

US 2021/0181079 A1    Jun. 17, 2021

Related U.S. Application Data

(60) Provisional application No. 62/948,294, filed on Dec. 15, 2019.

(51) Int. Cl.
| | | |
|---|---|---|
| *G01N 33/38* | (2006.01) | |
| *B28C 5/42* | (2006.01) | |
| *B28C 7/02* | (2006.01) | |
| *G01N 11/00* | (2006.01) | |

(52) U.S. Cl.
CPC ............ *G01N 11/00* (2013.01); *B28C 5/422* (2013.01); *B28C 7/026* (2013.01); *G01N 33/383* (2013.01); *G01N 2011/0006* (2013.01); *G01N 2011/0053* (2013.01)

(58) Field of Classification Search
CPC .......... G01N 2011/0053; G01N 33/383; B28C 7/026; B28C 5/422
See application file for complete search history.

(56) References Cited

U.S. PATENT DOCUMENTS

| | | | |
|---|---|---|---|
| 1,328,765 | A | 1/1920 | Robb |
| 1,410,126 | A | 3/1922 | Rosendahl |
| 1,781,549 | A | 3/1929 | Johnson |
| 2,273,750 | A | 11/1936 | Clagett, Jr. |
| 2,342,749 | A | 8/1941 | Maxon, Jr. |
| 2,543,883 | A | 9/1945 | Von Saspe |
| 3,160,393 | A | 12/1964 | Green |
| 3,237,437 | A | 3/1966 | Hilkemeier |
| 3,463,462 | A | 8/1969 | Sarff et al. |

(Continued)

FOREIGN PATENT DOCUMENTS

| | | |
|---|---|---|
| CA | 2246191 | 3/1999 |
| CA | 2503779 | 7/2005 |

(Continued)

OTHER PUBLICATIONS

Gaynor, Richard D.; "Understanding ASTM C94"; Copyright 1996.

(Continued)

*Primary Examiner* — Herbert K Roberts
(74) *Attorney, Agent, or Firm* — Robert H. Frantz

(57) ABSTRACT

Readings produced by an improved slump meter will be the consistent across a wide range of redi-mix units, regardless of the size of the load, make, model, age or condition of the redi-mix unit, therefore any mix consistency can be easily duplicated or created, by producing a common number for each mixer when running and empty, applying a conversion factor to raw hydraulic or electric motor work measurement data, and averaging and to stabilize the output reading on a refreshing period.

11 Claims, 3 Drawing Sheets

(56) References Cited

U.S. PATENT DOCUMENTS

| | | | |
|---|---|---|---|
| 3,731,909 A * | 5/1973 | Johnson | B28C 5/422 366/61 |
| 3,767,170 A | 10/1973 | Morgenstern | |
| 3,924,447 A | 12/1975 | Garrison | |
| 4,008,093 A | 2/1977 | Kitsuda et al. | |
| 4,318,177 A | 3/1982 | Rapp et al. | |
| 4,356,723 A | 11/1982 | Fay | |
| 4,544,275 A | 10/1985 | Hudelmaier | |
| 4,899,154 A | 2/1990 | Waitzinger et al. | |
| 5,352,035 A | 10/1994 | Macaulay et al. | |
| 5,527,387 A | 6/1996 | Anderson et al. | |
| 5,713,663 A | 2/1998 | Zandberg et al. | |
| 7,320,539 B2 | 1/2008 | Christenson et al. | |
| 8,727,604 B2 | 5/2014 | Compton et al. | |
| 8,746,954 B2 | 6/2014 | Cooley et al. | |
| 8,764,272 B2 | 7/2014 | Hazrati et al. | |
| 8,764,273 B2 | 7/2014 | Koehler et al. | |
| 8,858,061 B2 | 10/2014 | Berman | |
| 9,506,785 B2 | 11/2016 | Turk | |
| 2007/0263478 A1 | 11/2007 | Burch | |
| 2009/0037026 A1 * | 2/2009 | Sostaric | B01F 15/00207 700/265 |
| 2011/0077778 A1 | 3/2011 | Berman | |
| 2013/0021867 A1 | 1/2013 | Shimizu | |
| 2017/0028586 A1 * | 2/2017 | Jordan | E01C 19/1063 |

FOREIGN PATENT DOCUMENTS

| | | | |
|---|---|---|---|
| EP | 0126573 | A1 | 11/1984 |
| WO | 2010110814 | A1 | 9/2010 |
| WO | 2010111204 | A1 | 9/2019 |

OTHER PUBLICATIONS

Texas Dot; "Section 3: Concrete Plant Operation"; retrieved on Jan. 23, 2020 from http://onlinemanuals.txdot.gov/txdotmanuals/pdm/conc_plant_operation.htm.

CE-REF; Concrete Construction: ASTM C-94 Standard Specification for Ready-Mixed Concrete; retrieved on Jan. 23, 2020 from http://www.ce-ref.com/Construction/Ready_concrete/ASTM_C94.html.

Scaletron; "Concrete Batch Controls"; retrieved on Jan. 23, 2020 from https://scaletron.com.

Dougherty, William; "Ready-Mix Concrete"; retrieved on Jan. 23, 2020 from https://www.engr.psu.edu/ce/courses/ce584/concrete/library/construction/.

Cazacliu et al.; "New methods for accurate water dosage in concrete central mix plants"; Jan. 2008, from ResearchGate.

USPTO; Restriction Requirement dated May 21, 2020 in related, U.S. Appl. No. 16/804,634, filed Feb. 28, 2020.

Bollin, Neil E.; Election of Species submitted on Jul. 21, 2021 in related, U.S. Appl. No. 16/804,634, filed Feb. 28, 2020.

USPTO; First Office Action dated Jul. 30, 2020 in related, U.S. Appl. No. 16/804,634, filed Feb. 20, 2020.

Bollin; Respy to First Office Action dated Oct. 6, 2020 in related, U.S. Appl. No. 16/804,634, filed Feb. 28, 2020.

USPTO; Second Office Action dated Oct. 19, 2020 in related, U.S. Appl. No. 16/804,634, filed Feb. 28, 2020.

Concrete Controls; "Continuous automatic slump control . . . right to the pour." Retrieved on Nov. 21, 2019 from http://concretecontrols.com/DHSpage.html.

Concrete Controls; "Continuous slump control right to the Pour. Guaranteed!"; Hydraslump; Retrieved Nov. 21, 2019 from http://concretecontrols.com/DHSpage.html.

Concrete Controls; "Installation instructions for Dial-a-Matic & Semi-matic Hydra-slump Technical Information Sheet, DHS-94"; Retrieved on Nov. 21, 2019 from http://concretecontrols.com/DHSpage.html.

Environmental Expert; "Scale-Tron Inc. BatchTron—Model I—Little Batch Controller"; retrieved on Nov. 21, 2019 from https://www.environment-expert.com.

* cited by examiner

Mixer # _____

Slump and Load Size Data Log

| Wall | | Slip Form | | | | Hand Work | | | | Pump | |
|---|---|---|---|---|---|---|---|---|---|---|---|
| ID | TARGET | ID | TARGET | ID | TARGET | ID | TARGET | ID | TARGET | ID | TARGET | ID | TARGET | ID | TARGET | ID | TARGET |
| 101 | | 201 | | 301 | | 401 | | 501 | | 601 | | 701 | | 801 | | 901 | |
| 102 | | 202 | | 302 | | 402 | | 502 | | 602 | | 702 | | 802 | | 902 | |
| 103 | | 203 | | 303 | | 403 | | 503 | | 603 | | 703 | | 803 | | 903 | |
| 104 | | 204 | | 304 | | 404 | | 504 | | 604 | | 704 | | 804 | | 904 | |
| 105 | | 205 | | 305 | | 405 | | 505 | | 605 | | 705 | | 805 | | 905 | |
| 106 | | 206 | | 306 | | 406 | | 506 | | 606 | | 706 | | 806 | | 906 | |
| 107 | | 207 | | 307 | | 407 | | 507 | | 607 | | 707 | | 807 | | 907 | |
| 108 | | 208 | | 308 | | 408 | | 508 | | 608 | | 708 | | 808 | | 908 | |
| 109 | | 209 | | 309 | | 409 | | 509 | | 609 | | 709 | | 809 | | 909 | |
| 110 | | 210 | | 310 | | 410 | | 510 | | 610 | | 710 | | 810 | | 910 | |
| 111 | | 211 | | 311 | | 411 | | 511 | | 611 | | 711 | | 811 | | 911 | |
| 112 | | 212 | | 312 | | 412 | | 512 | | 612 | | 712 | | 812 | | 912 | |
| 113 | | 213 | | 313 | | 413 | | 513 | | 613 | | 713 | | 813 | | 913 | |
| 114 | | 214 | | 314 | | 414 | | 514 | | 614 | | 714 | | 814 | | 914 | |
| 115 | | 215 | | 315 | | 415 | | 515 | | 615 | | 715 | | 815 | | 915 | |

First Digit = Slump    Last 2 Digits = Load Size

DEVICE AND METHOD FOR CALIBRATING AND CORRELATING SLUMP IN A CONCRETE MIXER

The present patent application claims priority to U.S. provisional patent application 62/948,294, filed on Dec. 15, 2019, by Neil Bollin.

FIELD OF THE INVENTION

The invention generally relates to processes, devices and systems for timely completion of mixing of a batch of concrete according to a target slump or workability criteria.

BACKGROUND OF THE INVENTION

Stationary and mobile (truck-based) concrete mixing systems are widely used in construction of buildings, roads, bridges, dams, and the like. Slump, also referred to as workability, refers to the amount of deformation a certain prescribed amount and shape of concrete will exhibit when the form is removed while the concrete is still fresh and workable, before it is set or hardened. In the United States, there are at least two open standards from ASTM International (formerly known as American Society for Testing and Materials) and the American Association of State Highway and Transportation Officials (AASHTO) for the tools, fixtures, and processes for performing a slump test on fresh concrete. Additionally, some building codes provide various slump testing procedures, as well. Slump is one of several criteria commonly used to determine if a particular load of concrete is suitable to be used in the particular construction installation underway.

SUMMARY OF THE DISCLOSED EMBODIMENT(S)

Readings produced by an improved slump meter will be the consistent across a wide range of redi-mix units, regardless of the size of the load, make, model, age or condition of the redi-mix unit, therefore any mix consistency can be easily duplicated or created, by producing a common number for each mixer when running and empty, applying a conversion factor to raw hydraulic or electric motor work measurement data, and averaging and to stabilize the output reading on a refreshing period.

BRIEF DESCRIPTION OF THE DRAWINGS

The description of exemplary embodiments of the invention as set forth herein are illustrated by the drawings.

FIG. 2 illustrates an example user interface for reviewing and adjusting a data log for slump and load size according to at least one embodiment of the present invention.

DETAILED DESCRIPTION OF ONE OR MORE EXEMPLARY EMBODIMENT(S) OF THE INVENTION

Figure 1:
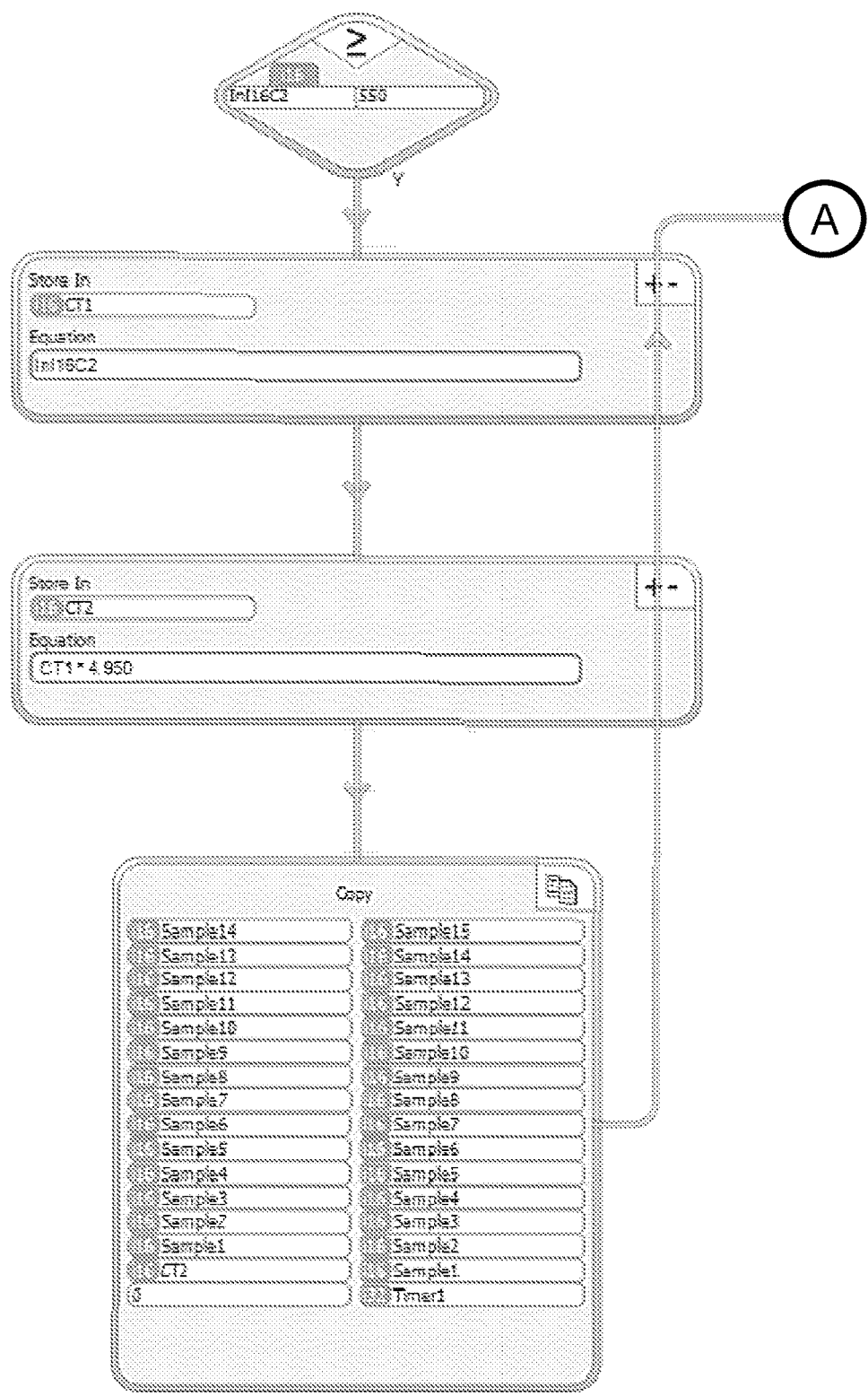
FIG. 1 illustrates a first portion of a logical flow suitable for performance by a microprocessor according to at least one embodiment of the present invention.

There are generally two production environments in which concrete is mixed. The first production environment is a "central mix concrete plant" where all minerals, fibers, water and other additives or mixed. The second production environment is a "redi-mix" environment which involves a truck-mounted mixer. Most of the redi-mix production environments also include a hydraulic pressure meter that measures the amount of work or energy required to turn the mixing drum, which is roughly correlated to an expected slump value of the concrete load being mixed therein. The inventor of the present invention has recognized a problem in the art not previously recognized or addressed by existing slump meters on the market. While existing slump meters provide for an approximate prediction of the slump of the concrete load at a given time, their accuracy and dependability (repeatability) are seriously lacking.

For example, when delivering redi-mix concrete to a road construction project in which a slipform is being used to create a 4" thick slab, the customer specification may allow for a slump of up to 0.5" or even 1.0" in some projects, which is an accuracy +/−25%. Tighter specifications are generally not specified because the existing slump meters would not allow enough trucks to deliver acceptable loads, and therefore, a lot of loads would be rejected and material wasted.

Therefore, there is a need in the art, recognized by the present inventor, for an improved redi-mix slump meter with greater accuracy and repeatability. Present day concrete producers with multiple mixers using currently available slump meters have a hard time duplicating the slump of designated a batch of concrete because of the many variables in equipment being used. All mixers because of design, size, power supply, wear, etc., produce a different output and is not a stable analog output. Most meters available today produce a different and unstable reading for a designated batch in different mixers.

To this end, embodiments of the present invention provide an improvement to slump meters which includes an ability to calibrate/correlate a slump meter that displays a common stable readout, such as a stabilized digital output, and which targets in the process of duplicating a designated batch of concrete to a designated common number, consistency, or slump on multiple mixers.

The prototype of the improved redi-mix slump meter is based upon the present inventor's Ultameter™ central mix monitoring system which has been proven in use in central mix systems. This slump meter was designed for a central mix concrete plant monitors and records in real time all the functions of the mixer including the slump, feed, mix, dump, return times and the plant discharge sequencing, all of which can be monitored from any remote computer or cell phone. In that process of designing this central mix slump meter, the present inventor developed processes to program all of the central mixers of different types and sizes to read the same values to yield the same concrete load parameters, thereby allowing operators to reliably interpret the readings without having to take into account individual differences between different central mix equipment, locations, ages, etc.

As such, at least one embodiment of the present invention includes providing certain improvements to the existing Ultameter [TM]. It is, therefore, useful on both electric and hydraulic driven concrete mixers for ¼ cubic yard thru 15 cubic yard mixers, for all makes and models of concrete mixers. It displays a modified digital reading produced from an analog signal obtained from a concrete mixer. The modified digital reading is the result of averaging and a delay in the signal output. The reading produced is more stable and easier to interpret by the operator. The result is the ability to duplicate the consistency or slump of multiple batches of concrete to a more precise measurement. It will be readily understood by those skilled in the relevant arts that the improvements according to the present invention may be equally well applied to other slump meters, either in analog or digital form, and that the disclosed example embodiment does not indicate a limitation regarding application of the present invention to other slump meters.

The present invention brings this benefit to redi-mix production environments, to allow the individual differences between different trucks, different hydraulic pumps, different hydraulic motors, different mixing drums and different load sizes with varying degrees of age and wear to be operated via a slump meter which avoids the operator having to mentally compensate for these individual differences in order to obtain a more precise slump characteristic of each concrete load. For example, an improved slump meter, especially on a redi-mix truck, might be designed to read 150 psi when the mixing drum is empty idle, to read 350 psi when the mixing drum contains a 7 yd load having a 3" slump, or to read 220 psi when the mixing drum contains a 4 yd load having a 5" slump. Embodiments according to the present invention calibrate and correlate a slump meter that is connected to a concrete mixer that can display a digital reading of a similar batch of freshly mixed concrete, regardless of size, make, or model of the concrete mixers.

The general procedure to provide these improvements comprises:

a. Produce a common number for each mixer when running and empty.
b. 2000/Raw data=conversion factor
c. Conversion factor× Raw Data=2000
d. 2000×15=30000 for averaging and to stabilize the output reading
e. 30000/75=400 the average and stable number
f. Average and stabilized number refreshed on meter every 1.25 seconds
g. 400−250=150=a common number for an empty running mixer This common number can be displayed in inches and fraction of an inch or by a 3-digit number whichever is preferred by the concrete producer In the production of concrete an algorithm needs to be created for the duplication of a batch concrete with the prescribed size of the batch and the slump requested.

This process can be created by using information from the actual testing of the slump of various size batches after the common empty number is established, such as:

Size of Batch in yds @ Slump in inches=Common number 8 yds @ 3" slump=? common number or
8 yds @ ? Slump=350 common number There are two reference points in establishing the prescribed slump of a batch of concrete being loaded in a ready-mix operation, one is at an idle speed and one is at the mixing speed of the mixing drum. The process created can include one or both as common number targets, such as:

8 yds @ 3" slump=Idle common number and/or mixing common number

The ready-mix version of the improved slump meter will display one or more of the following measurements and calculations:

1. Actual live number created by the loaded mixer
2. Enter Batch Id number (requested load size and Slump)
3. Idle Target number
4. Mixing target number
5. Log data Button
6. Enter truck number
7. Enter ticket number The ready-mix version of the improved slump meter will record one or more of the following measurements and calculations:

1. Truck Number
2. Batch ID Number (load size and slump)
3. Time loaded
4. Mix Time
5. Time when data logged
6. Slump idle target number
7. Actual Slump idle number when data logged
8. Ticket number By using this process, the raw data from the hydraulic or electric motor is converted to a common number, such as:

TABLE 1

Example Motor Power (Amps or PSI) to Slump Correlation

| Example: | Empty | Empty | Target # | Actual |
|---|---|---|---|---|
| Mixer A | 800 psi | 2000 | 150 | 0" Slump |
| Mixer B | 825 psi | 2000 | 150 | 0" Slump |
| Mixer C | 850 psi | 2000 | 150 | 0" Slump |

| | 8 yds | Idle Target # | Mixing Target # | Actual |
|---|---|---|---|---|
| Mixer A | 3000 | 350 | 425 | 3" Slump |
| Mixer B | 3000 | 350 | 425 | 3" Slump |
| Mixer C | 3000 | 350 | 425 | 3" Slump |

In this senereo the target # for each mixer to produce a 8 yd load with a 3" slump are all the same After the improved slump meter is calibrated for each installation on a particular redi-mix unit, the readings produced by the improved slump meter will be the same (consistent) across all redi-mix units, regardless of the size, make, model age or condition of the redi-mix unit. For example:

TABLE 2

Example Motor Power (Amps or PSI) to Slump Correlation Example:

| Mixer A | 10 cubic yd Hydralic mixer = 800 psi = empty = 2000 = 150 and 8 cubic yds @ 350 = 3" slump |
| Mixer B | 15 cubic yd electric mixer = 50 amps = empty = 2000 = 150 and 8 cubic yds @ 350 = 3" slump |

As such, the processes, devices and systems according to the present invention can be produced for the multitude of mix configurations needed and therefore any mix consistency can be easily duplicated or created.

An example slump chart 1000 for presentation on and modification through a portion of a computer user interface 100 according to the present invention is provided in FIG. 2, which was implemented through a spreadsheet program in a prototype embodiment.

Figure 3:
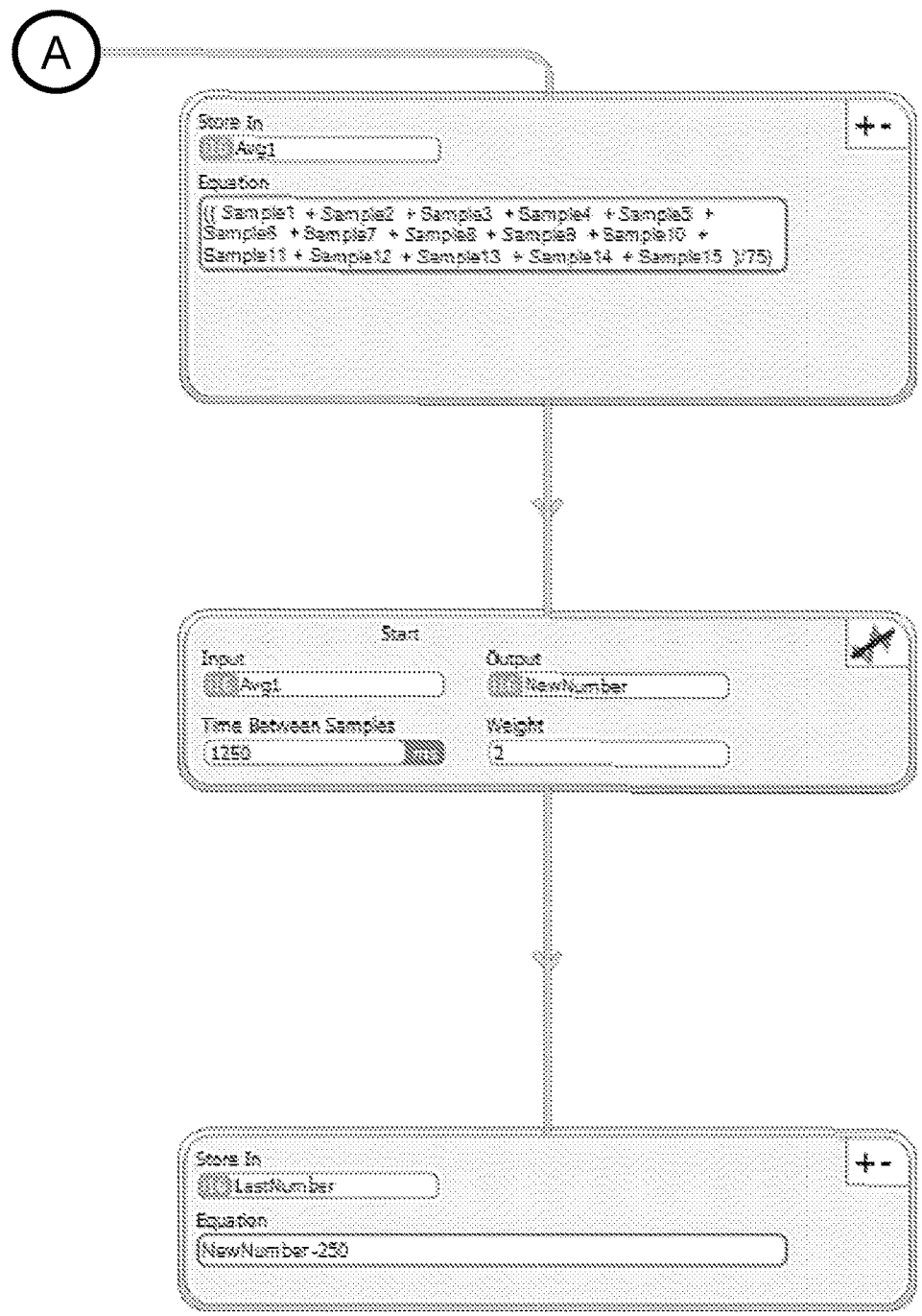
FIG. 3 illustrates a second portion of a logical flow of FIG. 1.

FIG. 1 and FIG. 3 provide an example logical process flow 1100 suitable for performance by a microprocessor according to at least one embodiment of the present invention, to synchronize slump indicators to produce the same or similar slump meter readings for an identical batch of concrete (in cubic yards and slump target) in concrete mixers of various types, sizes and shapes, including mobile (truck based) ready-mix units as wells a fixed-location (central mix) units.

CONCLUSION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless specifically stated otherwise.

The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

It will be readily recognized by those skilled in the art that the foregoing example embodiments do not define the extent or scope of the present invention, but instead are provided as illustrations of how to make and use at least one embodiment of the invention. The following claims define the extent and scope of at least one invention disclosed herein.

What is claimed is:

1. A process for automatically calibrating and correlating a slump meter that is connected to a concrete mixer to provide a user digital reading display of a similar batches of freshly mixed concrete, independent of concrete mixer size, make, or model, comprising:
    receiving, by a microprocessor, from a user entry, a Batch Identifier value;
    retrieving, by a microprocessor, from a motor power-to-slump correlation table stored in computer readable memory, at least one conversion factor corresponding to the specific concrete mixer and corresponding to the Batch Identifier value; and
    subsequent to the receiving the Batch Identifier value:
        receiving, by a microprocessor, from a specific concrete mixer, a plurality of real-time unadjusted concrete mixer drum motor hydraulic input pressure values measured periodically by a hydraulic pressure sensor at an input to the mixer drum motor;
        applying, by a microprocessor, the retrieved at least one conversion factor to each of the received concrete mixer drum motor hydraulic input pressure values to yield a plurality of real-time slump values independent of other operating conditions of the specific concrete mixer;
        periodically, averaging, by a microprocessor, over an averaging period, the plurality of real-time slump values; and
        periodically, refreshing a digital display, by a microprocessor, on a user interface, of the periodic averaged slump value.

2. The process as set forth in claim 1 wherein the second set of values comprises values received from a vehicle-mounted concrete mixer motor.

3. The process as set forth in claim 1 wherein the second set of values comprises values received from a stationary concrete mixer motor.

4. The process as set forth in claim 1 wherein the Batch Identifier value comprises at least one portion indicating a target slump value and at least one portion indicating a batch volume.

5. The process as set forth in claim 4 wherein the target slump indication portion comprises a target slump value in inches.

6. The process as set forth in claim 4 wherein the target slump indication portion comprises a target slump value in centimeters.

7. The process as set forth in claim 4 wherein the batch volume indication portion comprises a concrete load size in cubic yards.

8. The process as set forth in claim 4 wherein the batch volume indication portion comprises a concrete load size in cubic meters.

9. The process as set forth in claim 1 further comprising:
    receiving, by a microprocessor, from a user interface, a calibration update value; and
    modifying, by a microprocessor, in the motor power-to-slump correlation table stored in computer readable memory, at least one conversion factor corresponding to the Batch Identifier value and corresponding to the specific concrete mixer.

10. A computer program product for automatically calibrating and correlating a slump meter that is connected to a concrete mixer to provide a user digital reading display of a similar batches of freshly mixed concrete, independent of concrete mixer size, make, or model, comprising:
    a non-transitory computer-readable medium; and
    one or more program instructions stored by the non-transitory computer-readable medium which, when executed by a microprocessor, performing steps of:
        receiving from a user entry a Batch Identifier value;
        retrieving from a motor power-to-slump correlation table stored in computer readable memory, at least one conversion factor corresponding to the specific concrete mixer and corresponding to the Batch Identifier value; and
        subsequent to the receiving the Batch Identifier value:
            receiving, from a specific concrete mixer, a plurality of real-time unadjusted concrete mixer drum motor hydraulic input pressure values measured periodically by a hydraulic pressure sensor at an input to the mixer drum motor;
            applying, by a microprocessor, the retrieved at least one conversion factor to each of the received concrete mixer drum motor hydraulic input pressure values to yield a plurality of real-time slump values independent of other operating conditions of the specific concrete mixer;
            periodically, averaging, by a microprocessor, over an averaging period, the plurality of real-time slump values; and
            periodically, refreshing a digital display, by a microprocessor, on a user interface, of the periodic averaged slump value.

11. A system for automatically calibrating and correlating a slump meter that is connected to a concrete mixer to provide a user digital reading display of a similar batches of freshly mixed concrete, independent of concrete mixer size, make, or model, comprising:
    one or more microprocessors;
    a non-transitory computer-readable medium; and one or more program instructions stored by the non-transitory computer-readable medium which, when executed by a microprocessor, performing steps of:
receiving from a user entry a Batch Identifier value;
retrieving from a motor power-to-slump correlation table stored in computer readable memory, at least one conversion factor corresponding to the specific concrete mixer and corresponding to the Batch Identifier value; and
subsequent to the receiving the Batch Identifier value:
   receiving, from a specific concrete mixer, a plurality of real-time unadjusted concrete mixer drum motor hydraulic input pressure values measured periodically by a hydraulic pressure sensor at an input to the mixer drum motor;
   applying, by a microprocessor, the retrieved at least one conversion factor to each of the received concrete mixer drum motor hydraulic input pressure values to yield a plurality of real-time slump values independent of other operating conditions of the specific concrete mixer;
   periodically, averaging, by a microprocessor, over an averaging period, the plurality of real-time slump values; and
   periodically, refreshing a digital display, by a microprocessor, on a user interface, of the periodic averaged slump value.

* * * * *